United States Patent
Shtakelberg et al.

(12) 
(10) Patent No.: US 6,396,265 B1
(45) Date of Patent: May 28, 2002

(54) METHODS AND APPARATUS FOR NON-DESTRUCTIVE CONTROL AND FORECASTING CONCRETE STRENGTH

(75) Inventors: David Shtakelberg, Jerusalem; Shimon Boyko, Har Adar; Boris Wilge, Lapid, all of (IL)

(73) Assignee: Concrete Ltd., Jerusalem (IL)

( * ) Notice: Subject to any disclaimer, the term of this patent is extended or adjusted under 35 U.S.C. 154(b) by 0 days.

(21) Appl. No.: 09/517,275

(22) Filed: Mar. 2, 2000

(51) Int. Cl.$^7$ ................................. G01V 3/00
(52) U.S. Cl. .................. 324/300; 324/301; 324/306
(58) Field of Search ................. 324/300, 304, 324/307, 306, 309, 312, 318, 322, 303, 301

(56) References Cited

U.S. PATENT DOCUMENTS 5,672,968 A * 9/1997 Miller et al. ............... 324/300

OTHER PUBLICATIONS

Stewart C. Bushong "Magnetic Resonance Imaging physical and Biological Principles" 1996 Mosby–Year Boom Inc. Textbook; p. 476.*

* cited by examiner

*Primary Examiner*—Edward Lefkowitz
*Assistant Examiner*—Tiffany A. Fetzner
(74) *Attorney, Agent, or Firm*—G. E. Ehrlich Ltd.

(57) ABSTRACT

A method of measuring a strength of a capillary-porous chemically active material while hardening, the capillary-porous chemically active material including therein a liquid which undergoes metamorphosis and which is present in the capillary-porous chemically active material in different stages during curing, the method is effected by performing a high frequency, spin-echo nuclear magnetic resonance measurement of each stage of the liquid; and correlating the high frequency, spin-echo nuclear magnetic resonance measurement with a predetermined relationship between the strength and the high frequency, spin-echo nuclear magnetic resonance measurement.

28 Claims, 10 Drawing Sheets

METHODS AND APPARATUS FOR NON-DESTRUCTIVE CONTROL AND FORECASTING CONCRETE STRENGTH

FIELD AND BACKGROUND OF THE INVENTION

The present invention relates to methods and apparatus for measuring and predicting parameters of capillary-porous chemically active materials while and after curing. More particularly, the present invention relates to methods and apparatus for non-destructive control and prediction of concrete strength.

As used herein throughout the specification and in the claims section below the phrase "capillary-porous chemically active material(s)" includes cementitious substances, such as, but not limited to, cement, concrete, lime, gypsum, clay and the like.

Concrete, which is used for construction, must be analyzed to determine the structural properties parameters, particularly strength and other physical-mechanical properties of the final cured product, such as its potential for shrinkage.

Concrete is mainly a mixture of water, cement, sand, and gravel. It is known that the fraction of water at all stages of its preparation (e.g., mixing, compaction, curing and hardening), is one of the most crucial parameters, responsible for the strength of the final cured cement stone and concrete.

The water content in concrete appears in two main states (stages) during curing: chemically bound water and physically bound water. The relative water content in formed structure during curing permanently decreases, as a portion of the physically bound water interacts chemically with other concrete components and transforms into a solid phase, whereas another portion is evaporating away from the surface.

It is known that the amount of water that is physically bound has an important influence on the compressive strength and other physical-mechanical properties of concrete at all stages of its formation and utilization.

The traditional prior art methods for testing the strength of concrete require 28 days to complete. The builder usually does not or cannot delay construction 28 days to receive the test results. Rather, the construction usually continues in the hope that the concrete is sound. If in the final analysis, the concrete does not meet the standards, the building may have to be reinforced or even torn down, perhaps incurring major additional costs.

Thus, a method of quick analysis of concrete properties which predicts its final strength or measures the structure strength in situ while hardening, is very desirable.

In addition, when concrete is utilized as a strength bearing member, it would be useful to know when "shrinkage" of the concrete has been completed so as not to load the member prematurely, as the premature addition of load to bearing members could lead to cracking of the concrete structure. Shrinkage of cement stone and concrete is correlated to their moisture content. However, to a larger extent, the shrinkage value of cement stone and concrete depends on the size of pores and capillaries in the formed structure, in other words, on the energy level of physically-bound water, interacting with the solid phase.

There is a known method for determination of cement stone and concrete strength according to its porosity. To this effect, see, Roy D. M., Gouda G. R. Porosity—strength relation in porous materials with very high strength" J. Amer. Ceramic Soc., 53, No. 10, 1973, pp. 549–550. According to this method, the strength, R, is determined by:

$$R = -\frac{1}{k}\ln\frac{\pi}{\pi_0} \quad (1)$$

where $\Pi$ is the general porosity of the cement stone (concrete); $\Pi_0$ is the porosity at zero strength (R=0), which is approximately 60%; and k is a constant which equals 0.385×105 MPa.

There is an additional known method for determining cement stone and concrete strength, which is described by Powers T. C. "The physical structure and engineering properties of concrete" Port. Cem. Ass. Dept. Bul. 90, Chicago, July 1958.

According to this method, the volume of pores of the cement gel $V_g$, and the general volume of capillary space $V_k$ of the concrete are experimentally measured; whereas the strength is determined according to the following equation:

$$R = A\left(\frac{V_g}{V_g + V_k}\right)^n \quad (2)$$

where A and n are constants.

The change of the porosity parameters $V_g$ and $V_k$ of Equation 2 during process of hardening is well-supported by data from the literature. To this effect, see, for example, Sheikin A. E. "Structure durability and crack resistance of cement stone". Moscow, Stroyizdat, 1974, p. 191.

Table 1 below, for example, provides porosity related data for a cement stone having a water/cement (W/C) ratio of 0.7 during hardening.

TABLE 1

The change of general ($\Pi$), capillary ($\Pi_k$) and gel ($\Pi_g$) porosity of a cement stone at the process of hardening

| Time of hardening (days) | ($\Pi$) | $\Pi_k$ | $\Pi_g$ |
|---|---|---|---|
| 0 | 0.70 | 0.70 | — |
| 3 | 0.65 | 0.58 | 0.07 |
| 7 | 0.58 | 0.49 | 0.09 |
| 14 | 0.57 | 0.44 | 0.13 |
| 28 | 0.54 | 0.37 | 0.17 |

The difficulty and labor input associated with measuring the porosity of concrete and other capillary-porous chemically active materials (especially during hardening) are the shortcomings of the above mentioned methods.

This is due to the necessity to prepare a large quantity of twin-samples, each of which is tested at a particular stage of hardening.

Independent of the applied method for measuring porosity (e.g., nitric porometry, mercury porometry of low and high pressure, etc.), the tested sample should be completely dehydrated. This considerably complicates the testing method, increases its duration and considerably affects the properties of the tested material.

Since cement stone, concrete and other similar materials at any stage of hardening are poly-dispersed moist capillary-porous bodies, it is possible to avoid most of the above-mentioned shortcomings if concrete strength will be determined not by measuring its porosity, but rather by measuring the energy of physically bound water, which is contained in the pores and capillaries of its structure, which is indicative of its porosity and therefore of, for example, its strength.

Water (both in a liquid and gaseous form) is always in a state of thermodynamic equilibrium with the porous solid phase with which it interacts. Thus, the properties of water (viscosity, bounding energy, relaxation time, etc.) are changing in strict accordance with structure formation and, consequently, with the strength growth of the hardening material. To this effect, see, for example, Shtakelberg D. I. "Thermodynamics of water-silicate disperse materials structure-formation". Riga, Zinatne, 1984, p.200; and Shtakelberg D. I., Sytchov M. M. "Self-organization in disperse systems". Riga, Zinatne, 1990, p175; and Neville M. "Properties of concrete" Longman Scientific & Technical. NT., 1988, p779.

In a newly compressed cement paste, whose strength is minimal, e.g., in the order of $10^{-1}$ Mpa, practically all the water is distributed between the grains of a non-hydrated cement. The average distance between the grains is approximately 5–10 $\mu$m. At this state, the bond energy of water molecules and the material constitutes only a few kDz/mol.

While hardening, a portion of the water becomes chemically bound, i.e., transforms into a solid state with bond energy in the order of 1000 kDz/mol. Another portion of the water is contained in the pores of the formed cement gel. The size of these pores is less than $10^{-3}$ $\mu$m in diameter and the bond energy in this case is up to 50 kDz/mol. Another portion of the water occupies capillaries of a larger diameter ($10^{-2}$–$10^{-1}$ $\mu$m) with bond energy of up to 10–20 kDz/mol.

$T_2$ relaxation time of physically-bound water, contained in capillary-porous structure of chemically-active material changes in a very wide range: from 30–40 $\mu$sec (liquid of thin surface layers) up to 3×106 $\mu$sec (bulk water).

During subsequent stages of concrete structure hardening and until its final formation, the water distribution reaches a steady state in which 45–50% of the water is chemically bound, 40% of the water occupies the smaller pores of the cement gel, whereas 10–15% of the water occupies larger capillaries of the concrete structure.

Thus, information pertaining to the energy level of water contained in a concrete structure reflects its porosity, which, in turn reflects its strength. Therefore, it is possible to obtain a far more reliable correlation between the energy of water contained in a concrete structure and its strength.

It was already noted above that physically-chemically bound water in capillary-porous bodies always coexists in thermodynamic equilibrium with the solid phase. Nevertheless, all quality changes developing in cement stone and concrete during the process of structure forming and hardening, such as, chemical dispergation, colloidation, coagulation, crystallization, nucleation, development of inner cracks, etc., are almost immediately reflected by the energy of the liquid stage thereof. This is why, namely, the physically bound water is the most informative component of capillary-porous structures for quality evaluation of energetic level and consequently strength and other physical-mechanical properties.

There are various methods for quantitating (in terms of mass) and qualitating (in terms of energy) chemically and physically bound water in capillary-porous bodies. However, these adsorption methods, some of which are described in the references recited hereinabove, are rather complicated and labor-consuming. Moreover, performance of such measurements in areas of a high relative water vapor pressure ($\phi = p_i/p_s$) is complicated due to development of capillary condensation. In addition, adsorption methods are suitable solely for testing the samples of cement stone, concrete, etc., with a completely-formed or artificially stabilized structure.

Another method for studying the water content of concrete is neutron hydrometry (see, for example, The Troxler 4430 water/cement gauge). However, neutron hydrometry allows the sole obtainment of quantitative data (mass), whereas no qualitative data (energy) is collectable.

Methods for determining concrete strength and other physical-mechanical properties of concrete samples in situ using nuclear magnetic resonance (NMR) have been developed by the inventors.

NMR methods and apparatuses are well-known for over 50 years and have found an extensive usage in various fields including, but not limited to, oil fields (from oil exploration up to quality determination of petroleum products), food production, medicine, etc. Also, there are numerous and successful applications of NMR-technology in construction and in manufacturing of building materials, particularly for determination of cement qualities.

In order to understand the basics of these methods, a short description of NMR principles is now presented.

The NMR techniques involve placing a sample in a homogeneous magnetic field which is subjected to a pulse of radio-frequency radiation. There are charged particles in the sample which undergo a Larmor precession, i.e., a common rotation superposed by the magnetic field upon the motion of the system of charged particles, all the charged particles having the same ratio of charge to mass.

The absorption of energy by the sample is almost instantaneous. However, the loss of energy, i.e., the nuclear relaxation, is a type of exponential decay process which has time constants. Relaxation occurs when stimulated by local magnetic fields having components at the Larmor frequency, i.e., the angular frequency of the Larmor precession. (The precession and frequency are named after Sir Joseph Larmor, British physicist, who died in 1942.)

There are two distinct types of nuclear relaxation: spin-lattice relaxation and spin-spin relaxation.

Spin-lattice relaxation is an energy effect, and is the loss of the excess energy resulting from the excitation pulse to the surroundings, or lattice, as thermal energy. The time constant associated with spin-lattice relaxation is called $T_1$.

Spin-spin relaxation is an entropy effect, and is related to the loss of stage coherence induced by the excitation pulse. The time constant associated with spin-spin relaxation is called $T_2$.

There are various imaging methods which make use of either the spin-lattice or spin-spin relaxation. One is the constant-time imaging (CTI) method, a variation of which is the single-point imaging (SPI) method. Another method is called the spin-echo method, in which the radio-frequency field is applied in a sequence of two kinds of pulses, separated by a time interval $t_e$, and a decayed sequence of echoes are observed after each pulse.

U.S. Pat. No. 4,769,601 describes a method and apparatus for determining the extent of setting of cement and its strength as it sets by means of a pulsed NMR spectrometer. $T_1$ measurements are made while agitating the cement to simulate transportation and placement thereof.

There are articles in the scientific literature describing the use of NMR to study chemical dynamics of cement hydration. M. Bogdan et al., "Single-Point Imaging of Partially Dried, Hydrated White Portland Cement", J. of Magnetic Resonance, Series A, 116:266–269 discuss using the SPI method. The article states that "several groups have attempted to image water invasion of cured concrete samples using spin-echo imaging methods". These attempts are reported by J. Link et al., Magn. Reson. Imaging, 12:203, and F. Papavassillou et al., J. Am. Ceram. Soc., 76:2109. In regard to these attempts, Bogdan et al. state that "the spin-spin relaxation times of water in these dehydration experiments is only a few milliseconds, so the quality of traditional spin-echo images is disappointing". Bogdan et al. also state that in their study, "short echo-time, one-dimensional, spin-echo profiles of moist cured white-cement paste cylinders displayed poor signal-to-noise and geometric distortions from the ideal profile geometry".

Other scientific articles describing the use of NMR to study chemical dynamics of cement hydration, and which all do not use spin-echo methods or fail to successfully use spin-echo methods, include E. Laganas et al., "Analysis of Complex H-1 NMR Relaxation Measurements in Developing Porous Structures—A Study in Hydrating Cement", J. Applied Physics, 77:3343–3348; H. C. Gran, "Fluorescent Liquid Replacement Technique, A Means of Crack Detection and /Binder Ratio Determination in High-Strength Concretes", Cement & Concrete Res., 25:1063–1074; J. Kaufmann et al., "One-Dimensional Water Transport in Concrete", Materials & Structures, 28:115–124; S. Kwan et al., "Si-29 and Al-27 MASNMR Study of Stratlingite", J. Amer. Ceram. Soc., 78:1921–1926; R. A. Hanna et al., "Solid State Si-29 and Al-27 NMR and FTIR Study of Cement Pastes Containing Industrial Wastes and Organics", Cement & Concrete Res., 25:1435–1444; X. D. Cong et al., "Effects of the Temperature and Relative Humidity on the Structure of C-S-H Gel", Cement & Concrete Res., 25:1237–1245; S. U. Aldulaijan et al., "Si-29 MASNMR Study of Hydrated Cement Paste and Mortar Made With and Without Silica Fume", J. Amer. Ceram. Soc., 78:342–346; A. R. Brough et al., "A Study of the Pozzolanic Reaction by Solid State Si-29 NMR Using Selective Isotopic Enrichment", J. Materials Sci., 30:1671–1678; Y. Okada et al., "Influence of Starting Materials on the Formation of 1.1-NM-Tobermorite", J. Ceram. Soc. of Japan, 102:1148–1153; L. J. Schreiner et al., "NMR Line Shape-Spin-Lattice Relaxation Correlation Study of Portland Cement Hydration", J. Am. Ceram. Soc., 68[1]:10–16; R. Blinc et al., "NMR Relaxation Study of Adsorbed Water in Cement and Tricalcium Silicate Pastes", J. Am. Ceram. Soc., 61[1]:35– 39; and L. Barbic et al., "The Determination of Surface Development in Cement Pastes by NMR", J. Am. Ceram. Soc., 65[1]:25–30.

Thus, although using $T_1$ measurements to determine properties of concrete while hardening is well known, using spin-echo methods for making $T_2$ measurements have not been successful. As mentioned above, one of the main reasons for the lack of success in making $T_2$ measurements is the short relaxation times. However, the very same short $T_2$ relaxation times make it desirable to develop a method which uses $T_2$ measurements instead of $T_1$, because the concrete property information is obtained much quicker. The present invention provides such methods.

A method of using $T_2$ measurements for determining concrete strength, potential shrinkage, and readiness to accept coverings on concrete samples in situ is described in U.S. Pat. No. 5,672,968.

Column 1, lines 20–24 of U.S. Pat. No. 5,672,968 (hereinafter '968), recites:

The water in concrete appears in three states during curing—chemically bound, capillary bound, and free water. The relative fraction of water in these three states changes during curing with some of the water evaporating away from the concrete surface.

It will be appreciated in this respect that there are no "free water" in the structure of cement and concrete mixture (right after the beginning of hardening), and certainly not in the structure of the hardened concrete. According to the fundamental definitions of the theory of drying of capillary-porous bodies, free water is the water capable of moving under the influence of gravity forces. Such behavior of we ate is typical for capillaries, whose size is larger than $10^{-3}$ cm. (see, A. V. Likov "Theory of drying. Moscow, "Energija", 1968, p. 472. According to T. C. Powers "Structure and Physical Properties of Hardened Portland Cement Paste". J. Amer. Ceramic Soc., 41, pp. 1–6 (January 1958), the primary capillary porosity is determined by characteristic diameter of pores $(2.5-5.0)\times 10^{-4}$ cm, already at the stage of fresh-made concrete paste. This means that the water in the structure is found under the field of capillary forces from start, i.e., time zero, such that in effect there are no free water in concrete.

Furthermore, the relative water content in cement and concrete changes (decreases) primarily due to chemical bounding, and not as a result of water evaporation.

Column 1, lines 25–30 of '968, recites:

It is known that the amount of water that ends up chemically bound is highly correlated to the compressive strength of the concrete.

It will be appreciated in this respect that there is no, and cannot be, any correlation between the amount of chemically bound water and the hardness of concrete under pressure, because, only the level of capillary-porosity structure development and its properties determine the hardness of concrete and of other similar materials, which porosity is highly correlated to physically bound water and is not at all correlated the chemically bound water.

Column 3, lines 55–60 of '968 recites:

The present invention uses low frequency (approximately 1 MHz) NMR, which the inventors have found to provide the desired quality of spin-echo measurements.

This and similar recitations to the effect that the '968 technology uses low frequency (approximately 1 MHz) NMR appear in numerous other locations along the specification of '968, including, for example, on column 4, line 21, column 5, line 33 and column 7, line 2 and in the claims.

In all of these cases, the low-frequency (approximately 1 MHz) dimension of spin-echo NMR is claimed to be a distinguishing feature of the '968 technology. However, low frequency of the magnetic field is a significant disadvantage. In the experiments described in '968 (see FIGS. 2, 3 and 4 of '968) it is seen that the minimal possible time of $T_2$ relaxation, available for measuring, equals about 0.5 msec. Thus, more than 35% of water contained in the concrete structure remain "invisible". These 35%, however, are the fraction of water which are most adhered to the porous matrix and reflect its properties to the highest extent. Therefore, all of the conclusions and statements derived from these experiments are highly arguable and practically indemonstrable.

Column 4, lines 1–7 of '968 recites:

The water appears in the concrete in three different stages:
  a. Free water—$T_2$ relaxation time of 50–200 ms.
  b. Capillary bound water—$T_2$ relaxation time of 15–30 ms.
  c. Chemically bound water—$T_2$ relaxation time less than 0.2 ms.

See to this effect also column 6, lines 49–55 of '968. However, it is known that using $T_2$ measurement the relaxation time of free water, which is at all absent from cement paste and/or concrete structures, is in the order of 3 seconds, that of physically bound water (both in cement gel pores and in larger capillaries) is in the range of 30–100 $\mu$sec, and that of chemically bound water is in the range of 10–17 $\mu$sec.

To this effect see Mendelson K. S., Halperin W. P., Jehng J-Y., Song Y-Q. "Surface magnetic relaxation in cement pastes". Magnetic Resonance Imaging, Vol. 12., No. 2, pp. 207–208, 1994; Halperin W. P, Halperin W. P., Jehng J-Y., Song Y-Q. "Application of spin-spin relaxation time measurement of surface area and pore size distribution in a hydrating cement paste". Magnetic Resonance Imaging, Vol. 12, No. 2, pp. 169–173, 1994; Lahajnar G., Blinc R., Rutar V., Smoley V., Zupan cic 1., Kocuvan I., Ursic J. "On the use of pulse NMR techniques for the study of cement hydration". Cement and Concrete Research, Vol. 7, pp. 385–394, 1977; Milykovic L., Lasis D., MacTavish J. C., Pintar M. M., Blinc R., Lahajnar G. "NMR studies of hydrating cement: a spin-spin relaxation study of the early hydration stages". Cement and Concrete Research, Vol. 18, pp. 951–956, 1988.

It is evident from FIGS. 2–4 of '968 that all of the measurements therein were performed in the $T_2$ time intervals from approximately 0.5 msec to 1,300 msec. From the described distribution of water energy levels it is totally unclear what states of liquids were actually measured and which levels of liquids bonding with solid phase correspond to the peaks at values $T_2$=0.5–15 msec; $T_2$=30–50 msec; and $T_2$>200 msec. In other words, most of the measured $T_2$ interval, i.e., below 0.5 msec, which reflects the more tightly bound water in fine pores and capillaries was not measured, nor was it analyzed.

Capillary (physically) bound water is determined by the authors of '968 within an extremely narrow interval of $T_2$ relaxation times, i.e., $T_2$=15–30 msec. It is known that the porosity of cement stone and concrete changes in a very wide diapason from 15–100 Å (gel pores) up to $10^{-4}$ cm. To this effect, see, T. C. Powers "Structure and Physical Properties of Hardened Portland Cement Paste". J. Amer. Ceramic Soc., 41, pp. 1–6 (January 1958); and Neville A. M., "Properties of concrete" 3-rd Edition. Longman Scientific and Technical, N-Y, 1988). There are experimental data of $T_2$ values of physically bound water contained in various capillary-porous bodies as follows: fired-clay brick—$T_2$=360–620 μsec., sand-lime brick—$T_2$=1,700 μsec, mortar—$T_2$=2000 μsec. To this effect, see Pel L., Kopinga K., Bertram G., Lang G. "Water absorption in fired-clay brick observed by NMR scanning". J. Phys. D.: Appl. Phys. Vol. 28, pp. 675–680, 1995; and Pel L., Kopinga K., Brocken H. "Water transport in porous building materials". HERON 41, pp. 95–105, 1996.

Thus the values $T_2$=15–30 msec recited in '968 for capillary bound water corresponds to water present in large capillaries with a characteristic size of $10^{-4}$ cm. In turn, the whole broad spectrum of water states in capillary pores is left unmonitored or determined.

It is principally impossible to obtain a correlation between a particular, according to its quantity, concrete property, for example, strength, and spectrogram "amplitude of NMR-time relaxation $T_2$" (FIGS. 2 and 3 of '968), which is only a graphic illustration of some measured distribution. Moreover, character and form of the spectrograms, measured for the concrete of the same content at the same time of its hardening by means of various NMR spectrographs can differ. considerably, depending on the technical parameters of devices applied, and also depending on the specifics of processing of the measured experimental values (exponent value, etc.).

It will be appreciated that determination and prediction of concrete properties by means of correctional dependencies is possible only by means of juxtaposition of values of the given concrete property with specific numeral parameter values, determined according to the results of NMR-measurements.

The fact that the measured water content constitutes only about 65% (see FIG. 4 of '968) of the real content thereof directly results due to the insufficient resolving power of the device CoreSpec-1000 which was employed. This device, which was originally developed for handling geophysical problems (search for oil in the ground, etc.), does not allow to measure low relaxation times, $T_2$<300 msec, thus, about 35% of water remains "invisible". Consequently, the CoreSpec-1000 device is completely inapplicable for analysis of finely-dispersed capillary-porous systems such as cement stone and concrete.

There is, thus, still a widely recognized need for, and it would be highly advantageous to have, an operable and improved apparatus and methods for measuring and predicting properties of capillary-porous chemically active materials while hardening, devoid of the limitations of the prior art.

SUMMARY OF THE INVENTION

According to one aspect of the present invention there is provided a method for measuring a strength of a capillary-porous chemically active material while hardening, the capillary-porous chemically active material including therein water which undergoes stage metamorphosis and including a physically bound water portion, the method comprising the steps of performing a high at least 7 MHz, preferably at least 10 MHz, typically, between 10 MHz and 20 MHz, frequency, spin-echo nuclear magnetic resonance measurement of at least the physically bound water portion; and correlating the high frequency, spin-echo nuclear magnetic resonance measurement with a predetermined relationship between the strength and the high frequency, spin-echo nuclear magnetic resonance measurement.

According to another aspect of the present invention there is provided a method for determining a strength of a capillary-porous chemically active material while hardening, the capillary-porous chemically active material including therein water which undergoes stage metamorphosis and including a portion of physically bound water, the method comprising the steps of performing a spin-echo nuclear magnetic resonance measurement of at least the physically bound water portion; and correlating the spin-echo nuclear magnetic resonance measurement with a predetermined relationship between energy values of the physically bound water and the spin-echo nuclear magnetic resonance measurement, thereby determining the strength of the capillary-porous chemically active material while hardening.

According to yet another aspect of the present invention there is provided a method for measuring a strength of a capillary-porous chemically active material while hardening, the capillary-porous chemically active material including therein water which undergoes stage metamorphosis and including a physically bound water portion, the method comprising the steps of performing high at least 7 MHz frequency, spin-echo nuclear magnetic resonance measurements of at least the physically bound water at least at setting start point and at setting finish point; and extrapolating the strength based on a predetermined relationship between the strength and the high frequency, spin-echo nuclear magnetic resonance measurements.

According to still another aspect of the present invention there is provided a method for determining a strength of a capillary-porous lo chemically active material while hardening, the capillary-porous chemically active material including therein water which undergoes stage metamorphosis and including a portion of physically bound water, the method comprising the steps of performing spin-echo nuclear magnetic resonance measurements of at least the physically bound water at least at setting start point and at setting finish point; and extrapolating the strength based on a predetermined relationship between the strength and the spin-echo nuclear magnetic resonance measurements.

According to an additional aspect of the present invention there is provided a method of measuring a strength of a structure made of concrete while hardening, the concrete including therein physically bound water and chemically bound water, the method comprising the steps of performing an in situ, high at least 7 MHz frequency, spin-echo nuclear magnetic resonance measurement of at least the physically bound water; and correlating the high frequency, spin-echo nuclear magnetic resonance measurement with a predetermined relationship between the strength and the high at least 7 MHz frequency, spin-echo nuclear magnetic resonance measurement.

According to yet an additional aspect of the present invention there is provided a method of determining a strength of a structure made of concrete, the concrete including therein physically bound water and chemically bound water, the method comprising the steps of performing an in situ spin-echo nuclear magnetic resonance measurement of at least the physically bound water; and correlating the spin-echo nuclear magnetic resonance measurement with a predetermined relationship between energy values of the physically bound water and the spin-echo nuclear magnetic resonance measurement, thereby determining the strength of the structure made of concrete while hardening.

According to still an additional aspect of the present invention there is provided a method of predicting a strength of a structure made of concrete while hardening, the concrete including therein physically bound water and chemically bound water, the method comprising the steps of performing an in situ, a high at least 7 MHz frequency, spin-echo nuclear magnetic resonance (NMR) measurement of at least the physically bound water; and extrapolating the strength based on a predetermined relationship between the strength and the high frequency, spin-echo nuclear magnetic resonance measurement.

According to a further aspect of the present invention there is provided a method of predicting a strength of a structure made of concrete while hardening, the concrete including therein physically bound water and chemically bound water, the method comprising the steps of performing an in situ spin-echo nuclear magnetic resonance (NMR) measurement of at least the physically bound water; and extrapolating the strength based on a predetermined relationship between the strength and the spin-echo nuclear magnetic resonance measurement, a radio frequency shield is employed to substantially isolate the spin-echo nuclear magnetic resonance measurement from environmental noise.

According to yet a further aspect of the present invention there is provided an apparatus for measuring a strength of a structure made of a capillary-porous chemically active material, the capillary-porous chemically active material having a surface and including therein physically bound water and chemically bound water, the apparatus comprising a pulsed nuclear magnetic resonance generator for generating a sensitive volume in the concrete structure for performing therein an in situ, high at least 7 MHz frequency, spin-echo nuclear magnetic resonance measurement of at least the physically bound water in the capillary-porous chemically active material while hardening, the pulsed nuclear magnetic resonance generator including in an operative arrangement (a) a static magnetic field generator for generating a static magnetic field within the sensitive volume, the static magnetic field generator including at least one magnet so designed such that static magnetic field lines of the static magnetic field are disposable close (e.g., 5–30 mm, preferably 15–20 mm) and substantially perpendicular to the surface; (b) a radio frequency electromagnetic field generator for generating a radio frequency electromagnetic field, the radio frequency electromagnetic field generator including at least one radio frequency coil so designed such that electromagnetic field lines of the radio frequency electromagnetic field are disposable substantially parallel to the surface; and (c) a nuclear magnetic resonance receiver for receiving nuclear magnetic resonance signals form excitable nuclei in the capillary-porous chemically active material and for providing an output indicative of a strength of the capillary-porous chemically active materials.

According to still a further aspect of the present invention there is provided an apparatus for measuring a strength of a structure made of a capillary-porous chemically active material, the capillary-porous chemically active material having a surface and including therein physically bound water and chemically bound water, the apparatus comprising a pulsed nuclear magnetic resonance generator for generating a sensitive volume in the concrete structure for performing therein an in situ, spin-echo nuclear magnetic resonance measurement of at least the physically bound water in the capillary-porous chemically active material while hardening, the pulsed nuclear magnetic resonance generator including in an operative arrangement (a) a static magnetic field generator for generating a static magnetic field within the sensitive volume, the static magnetic field generator including at least one magnet so designed such that static magnetic field lines of the static magnetic field are disposable close and substantially perpendicular to the surface; (b) a radio frequency electromagnetic field generator for generating a radio frequency electromagnetic field, the radio frequency electromagnetic field generator including at least one radio frequency coil so designed such that electromagnetic field lines of the radio frequency electromagnetic field are disposable substantially parallel to the surface; and (c) a nuclear magnetic resonance receiver for receiving nuclear magnetic resonance signals form excitable nuclei in the capillary-porous chemically active material and for providing an output indicative of a strength of the capillary-porous chemically active materials.

According to further features in preferred embodiments of the invention described below,.each of the at least one radio frequency-coil is shaped as a frustum having a smaller base and a wider top and is disposable with its longitudinal axis perpendicular to the surface and having its smaller base disposable on the surface.

According to still further features in the described preferred embodiments the at least one magnet includes a horseshoe magnet having its opening disposable against the surface.

According to still further features in the described preferred embodiments the at least one magnet includes one larger and one smaller horseshoe magnets.

According to still further features in the described preferred embodiments the at least one magnet has a butterfly-type cross section.

According to still further features in the described preferred embodiments the at least one magnet includes an upside-down "T"-bar magnet.

The present invention successfully addresses the shortcomings of the presently known configurations by providing an apparatus and method for measuring and predicting properties of capillary-porous chemically active materials while hardening.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
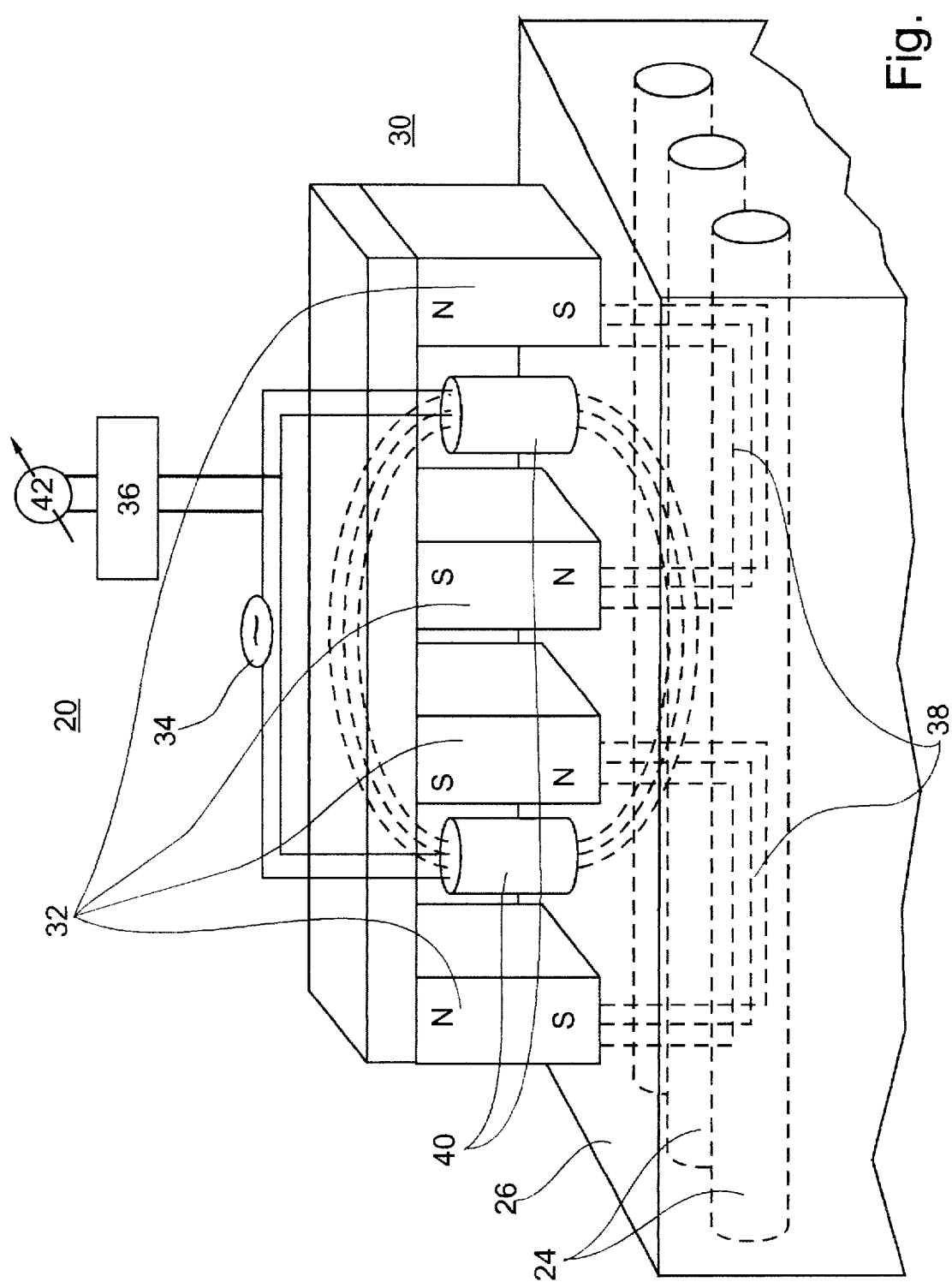
FIG. 1 is a simplified cross sectional view of an apparatus for measuring a property of a structure made of a capillary-porous chemically active material according to one embodiment of the present invention.

The present invention is of methods and apparatus which can be used for measuring and predicting properties of capillary-porous chemically active materials while hardening. Specifically, the present invention can be used for predicting the final formation strength of capillary-porous chemically active materials while hardening. Most specifically, the present invention provides methods and apparatus for non-destructive control and forecasting of concrete strength.

The principles and operation of a method and apparatus according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

According to a preferred embodiment of the present invention, strength determination of concrete or other chemically-active capillary-porous materials is performed as follows:

At any particular time point during hardening of concrete, a high frequency, e.g. at least 7 MHz, spin-echo NMR measurement is performed.

Based on the obtained NMR spectrogram, the quantity of physically-bound water (at substantially all energy levels) and the overall energy of such water are determined.

Concrete strength is thereafter determined based on a predetermined relationship between strength and results of high frequency (e.g., at least 7 MHz) spin echo NMR-measurements.

According to a preferred embodiment of the present invention, the predicted strength of concrete or of any other capillary-porous chemically active material undergoing a process of hardening is determined while executing the following steps:

A first high frequency (at least 7 MHz) spin echo NMR measurement is performed and the energy of physically bound water at the moment of setting start (Ea) of cement or concrete is determined in accordance with ASTM C-191 "Standard Test Method for Time of Setting of hydraulic cement by Vicat Needle".

A second high frequency (at least 7 MHz) spin echo NMR measurement is performed and the energy of physically bound water at the moment of setting finish (Ei) of cement or concrete is determined in accordance with ASTM C-191.

On the basis of these NMR measurements, which are performed at times of setting start and setting finish, a relation Ea/Ei of RF-field absorption of energy of physically bound water is determined.

In accordance with a preferred embodiment of the present invention, a property of concrete, such as strength, viscosity or any other property, is than determined based on a predetermined relationship between that property and the corresponding energy relation Ea/Ei of the physically-bound water.

The high frequency (e.g., at least 7 MHz), spin-echo NMR method according to the present invention makes use of water found in the concrete.

Thus, the present invention provides a method of determining concrete strength and other physical-mechanical properties thereof on concrete samples in situ using nuclear magnetic resonance (NMR). An analysis of concrete performed in accordance with the method of the present invention takes a few hours instead of the 28 days of the prior art, thus providing reliable and quick information to the builder and virtually eliminating any financial risk.

The embodiments and examples of the present invention are described herein mostly with reference to the curing of concrete. However, it is appreciated that the present invention is applicable not only to curing of concrete, but to any capillary-porous chemically active material which contains a liquid which undergoes metamorphosis during hardening, and in which a spin-echo NMR measurement may be made of the different stages of the liquid while hardening.

The present invention uses high frequency (approximately at least 7 MHz) NMR, which provides the desired quality of spin-echo measurements and can detect $T_2$ relaxation times of most, say at least 85%, preferably at least 90%, more preferably, at least 95%, most preferably, substantially all (e.g., 98–100%) of the physically bound water and optionally the chemically bound water in curing concrete.

The present invention makes use of the NMR spin-echo method to analyze the concrete. By analyzing the NMR signal from a fresh mixture of concrete by means of the $T_2$ relaxation time distribution, one can estimate properties, such as strength, potential shrinkage, or readiness to accept coverings, of the final cured concrete by measuring the metamorphosis of the water that is trapped in the concrete mixture as a function of time.

As already stated in the Background section above, the water appears in concrete in two different stages (i) physically bound water, a portion thereof is contained in the pores (less than $10^{-3}$ $\mu$m in diameter) of the formed cement gel and having a bond energy of up to 50 kDz/mol and $T_2$ relaxation time of about 50–100 $\mu$sec, whereas another portion thereof occupies capillaries of a larger diameter ($10^{-2}$–$10^{-1}$ $\mu$m) with bond energy of up to 10–20 kDz/mol and $T_2$ relaxation time of 100–300 $\mu$sec; and (ii) chemically bound water which transforms into a solid state with bond energy in the order of 1000 kDz/mol and $T_2$ relaxation time of about 10–17 $\mu$sec.

Thin films of surface moisture having a thickness of 1–2 molecular layers (about (3–6)×10–4 $\mu$m) constitute a specific part of the physically-bound water. This water has anomalous properties as is compared to a body of water: density of approximately 1.1 g/cm$^3$, viscosity in the order 10 cantiStock (cSt), and it is removable from the surface at temperatures around 250–300 C.°.

It is also known that relaxation time of this water fraction is $T_2$=30–40 $\mu$sec (see Mendelson K. S., Halperin W. P., Jyn-Yuar Jehng, Yi-Qiao Song. Surface magnetic relaxation in cement pastes. Magnetic Resonance Imaging, vol.12, No. 2, pp. 207–208, 1994).

This water fraction gives the most interesting information regarding the structure development of the hardening chemically-active capillary-porous material. Growth in quantity of this water is directly related to the formation of the new interior surfaces of a developing structure.

The formation of new surfaces, their quantity in units of material, their volume, and the following relation directly determine the increase in strength. Thus, knowing the quantity of this water fraction and on the basis of predetermined relationship between the results of NMR-measurements and strength, it is possible to determine concrete strength at any state.

There is thus provided in accordance with one aspect of the present invention, a method of measuring a property of a capillary-porous chemically active material while hardening, the capillary-porous chemically active material including therein a liquid which undergoes metamorphosis and which is present in the capillary-porous chemically active material in different stages during curing. The method according to this aspect of the present invention is effected by implementing the following method steps, in which, in a first step, a high frequency (e.g., at least 7 MHz), spin-echo nuclear magnetic resonance (NMR) measurement of each stage of the liquid is performed, whereas in a second step of the method the NMR measurement is correlated with a predetermined relationship between the property and the NMR measurement.

According to another aspect of the present invention there is provided, a method of predicting a property of a capillary-porous chemically active material while hardening, the capillary-porous chemically active material including therein a liquid which undergoes metamorphosis and which is present in the capillary-porous chemically active material in different stages during curing. The method according to this aspect of the present invention is effected by implementing the following method steps, in which, in a first step, a high frequency (e.g., at least 7 MHz), spin-echo nuclear magnetic resonance (NMR) measurement of each stage of the liquid is performed, whereas in a second step the property based on a predetermined relationship between the property and the NMR measurement is extrapolated.

According to yet another aspect of the present invention there is provided, a method of measuring a property of a structure made of concrete, the concrete including therein physically bound water and chemically bound water. The method according to this aspect of the present invention is effected by implementing the following method steps, in which, in a first step, an in situ, high at least 7 MHz frequency, spin-echo nuclear magnetic resonance (NMR) measurement of at least the physically bound water and optionally also the chemically bound water are performed, whereas, in a second step, the NMR measurement is correlated with a predetermined relationship between the property and the NMR measurement.

According to still another aspect of the present invention there is provided, a method of predicting a property of a structure made of concrete, the concrete including therein physically bound water and chemically bound water. The method according to this aspect of the present invention is effected by implementing the following method steps, in which, in a first step, an in situ, high frequency (e.g., at least 7 MHz), spin-echo nuclear magnetic resonance (NMR) measurement of at least the physically bound water and optionally also the chemically bound water are performed, whereas, in a second step, the property based on a predetermined relationship between the property and the NMR measurement is extrapolated.

In accordance with preferred embodiments of the present invention, an RF shield is employed to substantially isolate the NMR measurement from environmental noise, preferably the high frequency is approximately at least 7 MHz, whereas the property may be for example, strength, potential shrinkage, or readiness to accept coverings.

FIGS. 1–4 illustrate several embodiments of an apparatus according to the present invention, which is referred to hereinbelow as apparatus 20 and which can be used to effect the methods according to the present invention.

Apparatus 20 according to the present invention thus serves for measuring a property of a structure made of capillary-porous chemically active material 24 which has a surface 26 and which includes therein physically bound water and chemically bound water. The structure may additionally include a steel armature.

Apparatus 20 includes a pulsed nuclear magnetic resonance generator 30. Generator 30 serves for generating a sensitive volume in concrete structure for performing therein an in situ, high frequency (e.g., at least 7 MHz), spin-echo nuclear magnetic resonance measurement of at least the physically bound water present in a capillary-porous chemically active material 24 while hardening.

According to preferred embodiments of the present invention, pulsed nuclear magnetic resonance generator 30 includes, in an operative arrangement, a static magnetic field generator 32, a radio frequency electromagnetic field generator 34 and a nuclear magnetic resonance receiver 36.

Static magnetic field generator 32 serves for generating a static magnetic field 38 within the sensitive volume of structure.

Figure 2:
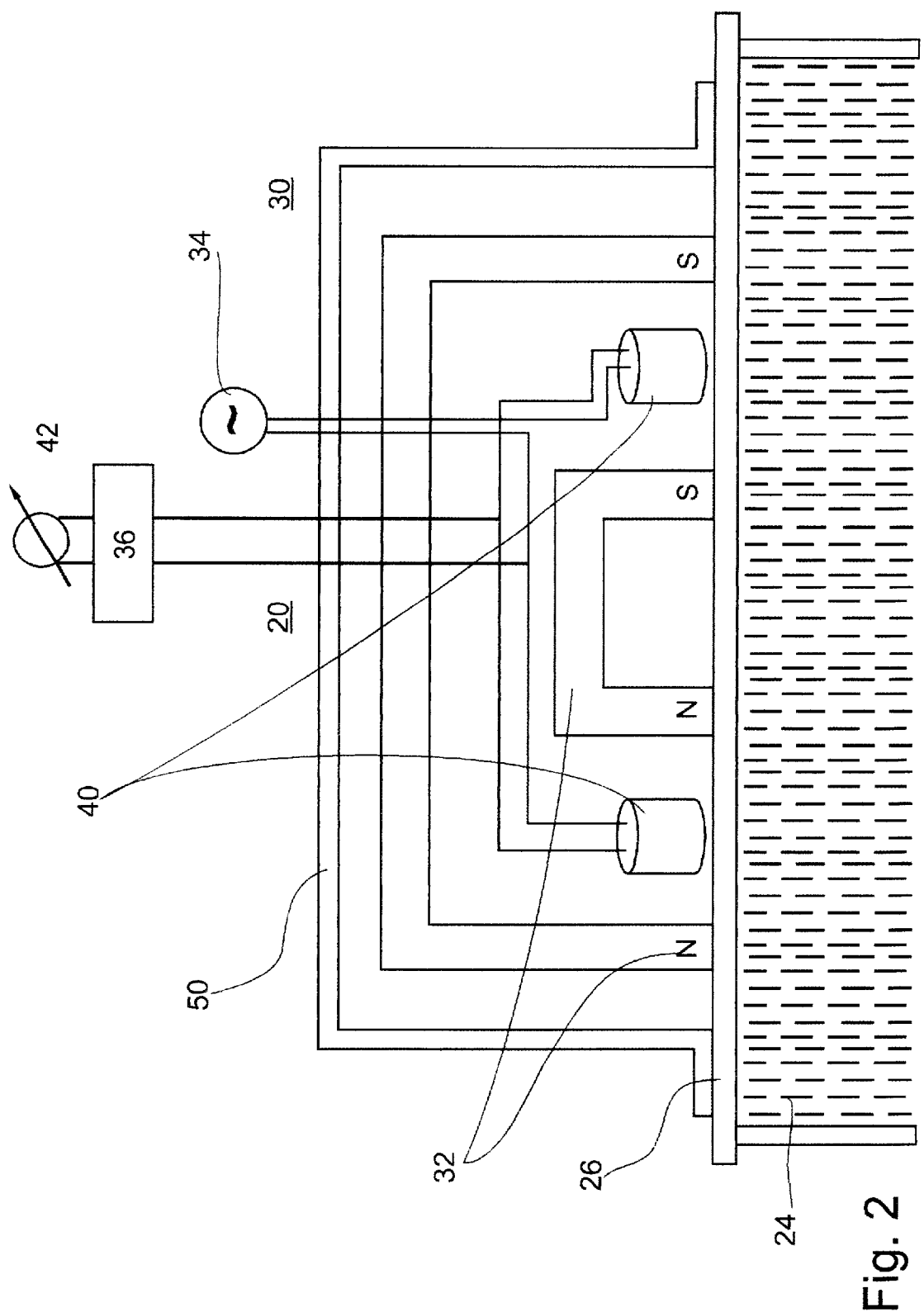
FIG. 2 is a simplified cross sectional view of an apparatus for measuring a property of a structure made of a capillary-porous chemically active material according to another embodiment of the present invention.
Figure 3:
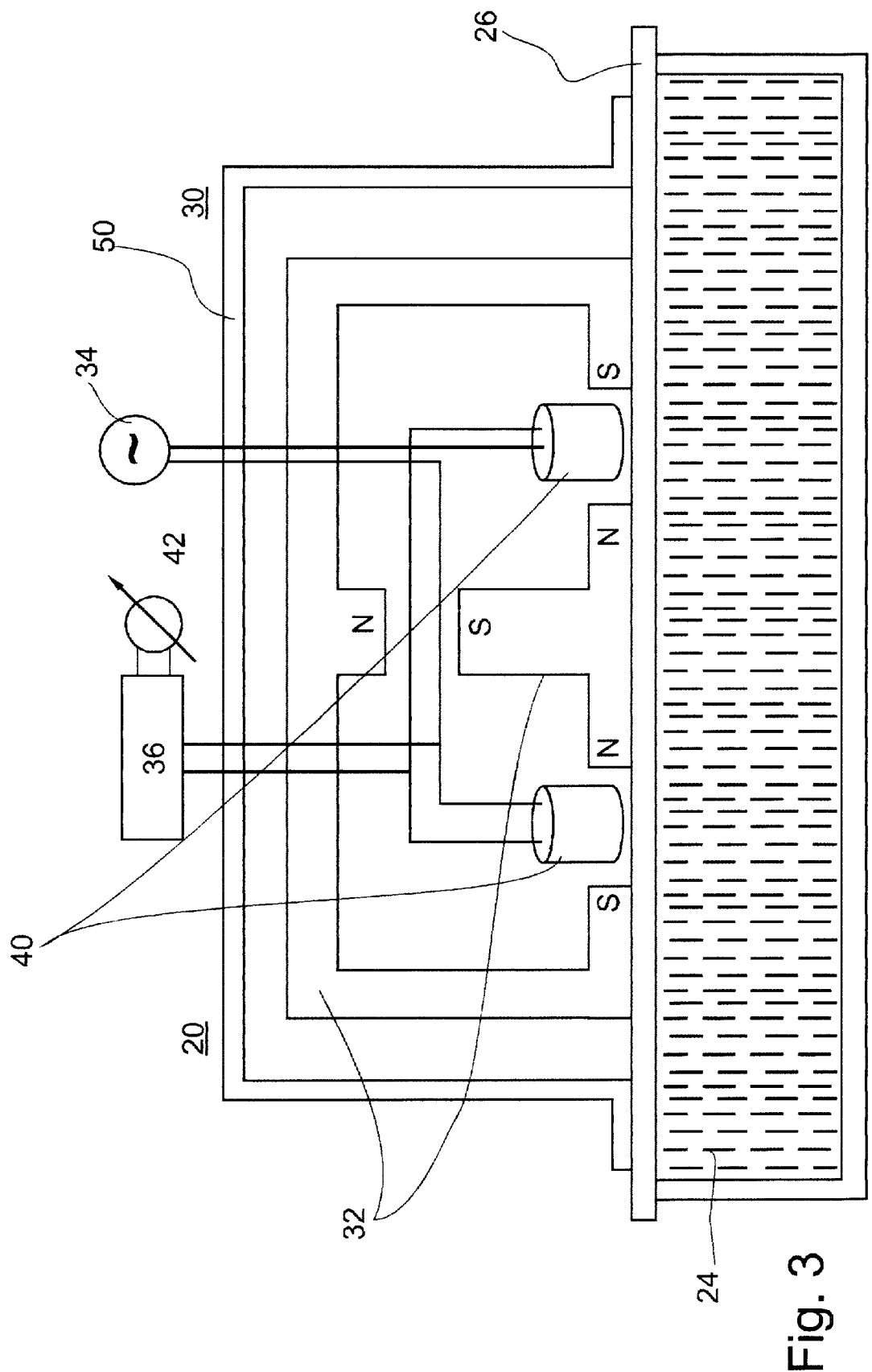
FIG. 3 is a simplified cross sectional view of an apparatus for measuring a property of a structure made of a capillary-porous chemically active material according to still another embodiment of the present invention.
Figure 4:
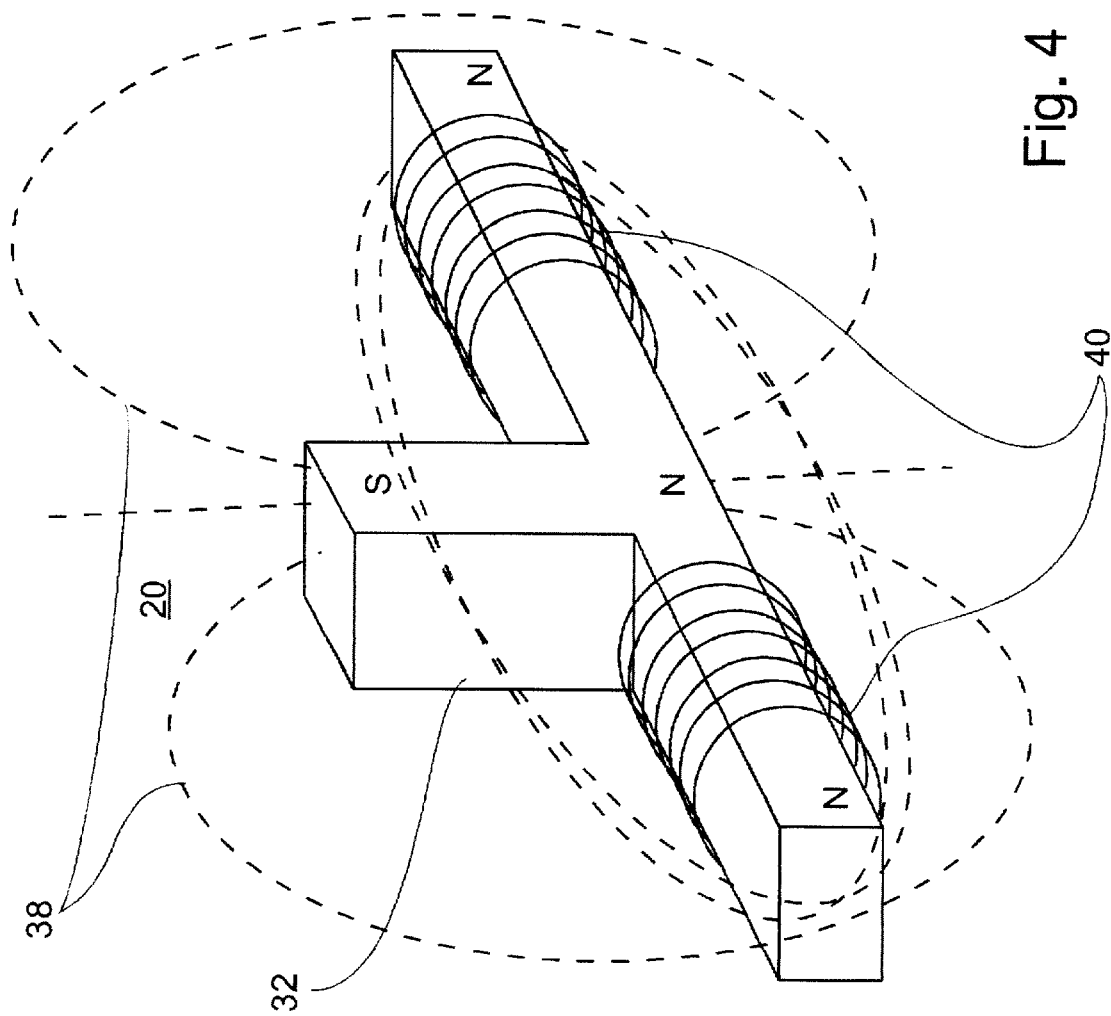
FIG. 4 is a simplified perspective view of a "T"-type magnet and a radio frequency coil placed therein, which are employed with the apparatus for measuring a property of a structure made of a capillary-porous chemically active material according to still another embodiment of the present invention.

In the configuration of FIGS. 1–3, two magnets are shown, whereas in that of FIG. 4, a single magnet is shown.

Magnet(s) 32 are so designed such that static magnetic field lines of the static magnetic field are disposable close and substantially perpendicular to surface 26.

In the configurations of FIGS. 1–2, at least one of magnet 32 is a horseshoe magnet having its opening disposed against surface 26. In FIG. 1, two horseshoe magnets 32 are employed, arranged side by side. In FIG. 2, two horseshoe magnets are employed, the smaller thereof is disposed between the poles of the larger one. As shown in FIG. 3, according to another preferred embodiment, one of magnets 32 has a butterfly-type cross section, whereas another has an upside-down "T"-bar cross section. As shown in FIG. 4, a single magnet which has an upside-down "T"-bar cross section can be employed. Other configurations are also envisaged.

Radio frequency electromagnetic field generator 34 serves for generating a radio frequency electromagnetic field. Radio frequency electromagnetic field generator 34 thus includes at least one radio frequency coil 40. In the configurations of FIG. 1–4, two coils 40 are shown.

Coil(s) 40 are so designed such that electromagnetic field lines of radio frequency electromagnetic field are disposable substantially parallel to surface 26.

In the embodiments shown in FIGS. 1–3 coil(s) 40 are disposed between the poles of magnet(s) 32.

Nuclear magnetic resonance receiver 36 serves for receiving nuclear magnetic resonance signals form excitable nuclei in capillary-porous chemically active material 24 and for providing an output indicative of a property of capillary-porous chemically materials 24 via data processing, as indicated by box 42.

A radio frequency shield 50 (FIG. 2) is preferably employed to substantially isolate the high frequency, spin-echo nuclear magnetic resonance measurement from environmental noise. Shield 50 preferably also serves as a housing which houses other components of apparatus 20.

Additional objects, advantages, and novel features of the present invention will become apparent to one ordinarily skilled in the art upon examination of the following example, which is not intended to be limiting. Additionally, each of the various embodiments and aspects of the present invention as delineated hereinabove and as claimed in the claims section below finds experimental support in the following example.

EXAMPLE

Thus, reference is now made to the following example, which together with the above descriptions, illustrate the invention in a non limiting fashion.

According to the present invention, high frequency (e.g., at least 7 MHz), spin-echo nuclear magnetic resonance (NMR) is used to control and/or monitor the structural solidity of cement stone, concrete and other capillary-porous chemically active materials.

As shown herein, high frequency (e.g., at least 7 MHz), spin-echo nuclear magnetic resonance (NMR) allows to unambiguously determine the distribution on physically bound water in the structure according to water energy levels, characterized by corresponding values of $T_2$ relaxation times while hardening.

The implementation of the high frequency (e.g., at least 7 MHz), spin-echo nuclear magnetic resonance (NMR) method according to the present invention is feasible due to existence of the following (i) linear relation between the quantity of physically bound water in a concrete structure and the amplitude of NMR measurement generated by this water; and (ii) functional dependency between the energy state of water, as determined by the overall energy E of absorption of the RF field and the $T_2$ relaxation time. This dependency, according to A. Abraham (Principles of Nuclear Magnetism, Oxford, Clarendon Press, 1996), is:

$$E = \frac{\hbar}{4kT} \omega^2 \cdot \gamma^2 \cdot H_1^2 \cdot N \cdot T_2 \qquad (3)$$

where h equals $6.63 \cdot 10^{-34}$ J/sec (Plank's constant); $\omega_0 \approx \omega_1$ are the Larmor frequency and the rotating RF-field frequency, accordingly; $\gamma$ is a gyroscopic relation; $H_1$ is the tenseness of the magnetic field of the inner-spinning magnet; k equals $1.38 \cdot 10^{-23}$ J/° K (Boltsman's constant); and T is the temperature (° K).

Since all of the parameters in equation (3), except for the quantity of protons, N, of the $T_2$ relaxation time, $T_2$, are either general constants or constants characterizing the device, then equation (3) can be written as:

$$E = \text{const} \cdot N \cdot T_2 \qquad (4)$$

where $$\text{constant} = \frac{\hbar^2}{4kT} \omega^2 \cdot \gamma^2 \cdot H_1^2 \qquad (5)$$

In subsequent calculations the following values were employed: $\omega = 6.28 \cdot 10^7$ sec-1; $\gamma = 2.67 \cdot 10^4$ sec$^{-1} \cdot$ersted$^{-1}$; $H_1 = 10^2$ ersted. These values allow to determine the overall energy of absorption of the RF-field in a time unit as:

$$E = 7.64 \cdot 10^{-19} \cdot N \cdot T_2 (J/\text{sec}) \qquad (6)$$

Since 1 mol of $H_2O$ contains $1.2 \cdot 10^{21}$ protons, then, while measuring the $T_2$ relaxation time according to equation (6), it is always possible to calculate the overall energy of absorption of the RF-field for all of the mass of the physically-bound water, found in the analyzed structure.

The method of determining and forecasting the strength of concrete and other capillary-porous chemically active materials according to the present invention was realized in practice on samples of standard cement-sand (C:S) mixture, manufactured and conventionally tested in accordance with the European Standard EN 196-1987, Part 1: Methods of testing cement. Determination of strength.

To determine concrete's strength, a series of sample-beams of a standard size (40×40×160 mm) and content (C:S=1:3 with water-cement ratio W/C=0.5) were manufactured. An overall quantity of 10 series, 3 samples in each series, were manufactured. The standard samples were produced using a cement marked "250" of 2 Israeli cement plants: Ramla and Har-Tuv (Nesher company). Compression strengths were determined at days 1 (in addition to the requirements of standard EN 196), 3 and 28.

During preparation of each standard sample (water:cement:sand ratio of 3.33:6.66:20, respectively), 30 gram samples of each were collected and placed into the working volume of an NMR-analyzer— "Minispec mq 10" product of Bruker company having a working frequency of 10 MHz.

Figure 6:
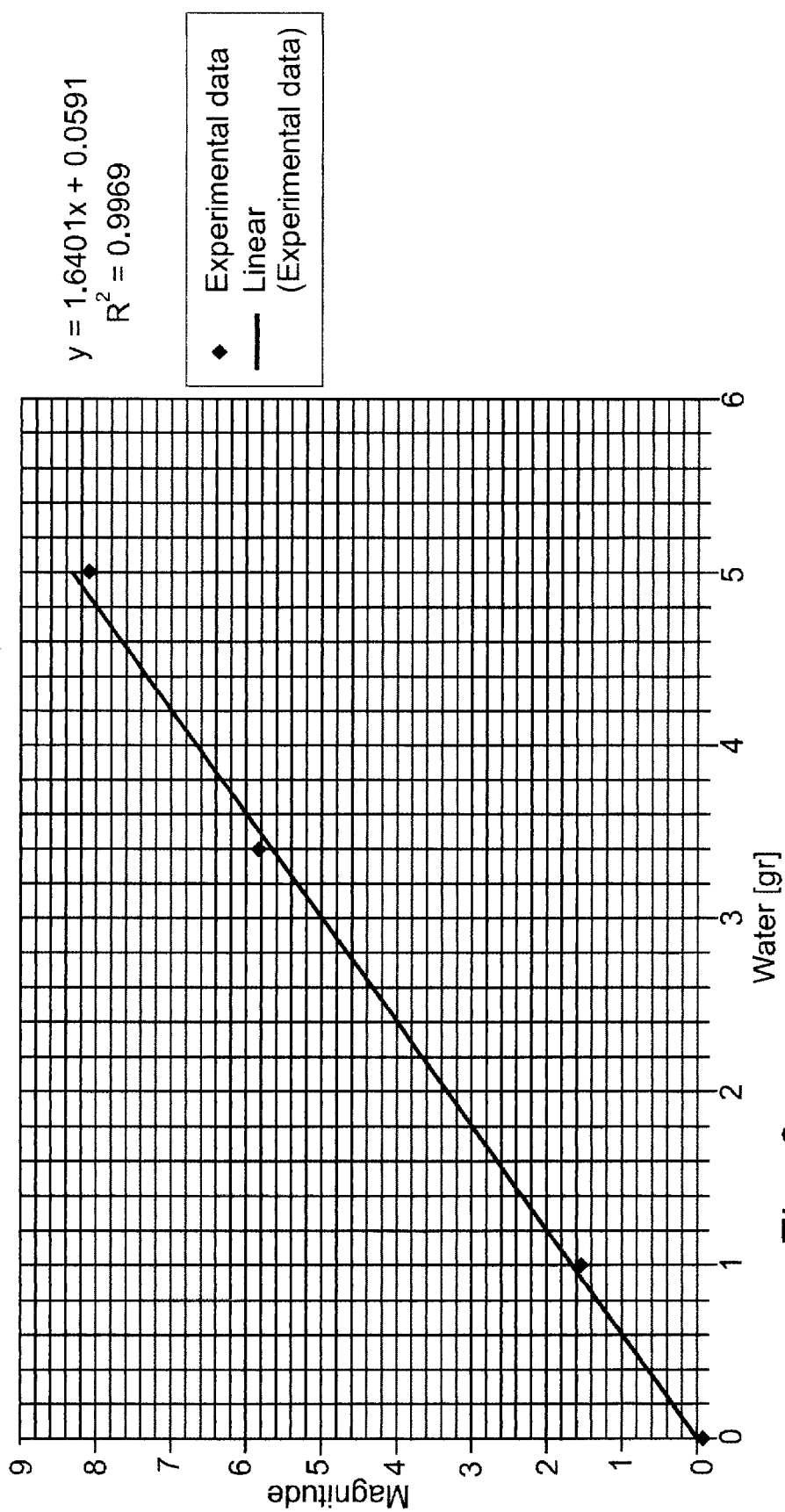
FIG. 6 shows a commutative plot demonstrating the physically bound water content, as determined by $T_2$ relaxation time, at various stages of concrete hardening.

NMR-measurements of $T_2$ relaxation time and masses of physically-bound water were performed at 2 (see, ASTM C-191 "Standard Test Method for Time of Setting of Hydraulic Cement by Vicat Needle"), 24. 72 and 672 hours. As an example, FIG. 6 presents the results obtained for concrete manufactured based on cement derived from the plant in Ramla.

It is evident that the NMR device employed allows to measure rather short $T_2$ relaxation times, $T_2$=40–50 $\mu$sec, which allows "to see" practically all of the physically-bound water in the analyzed structure.

Figure 7:
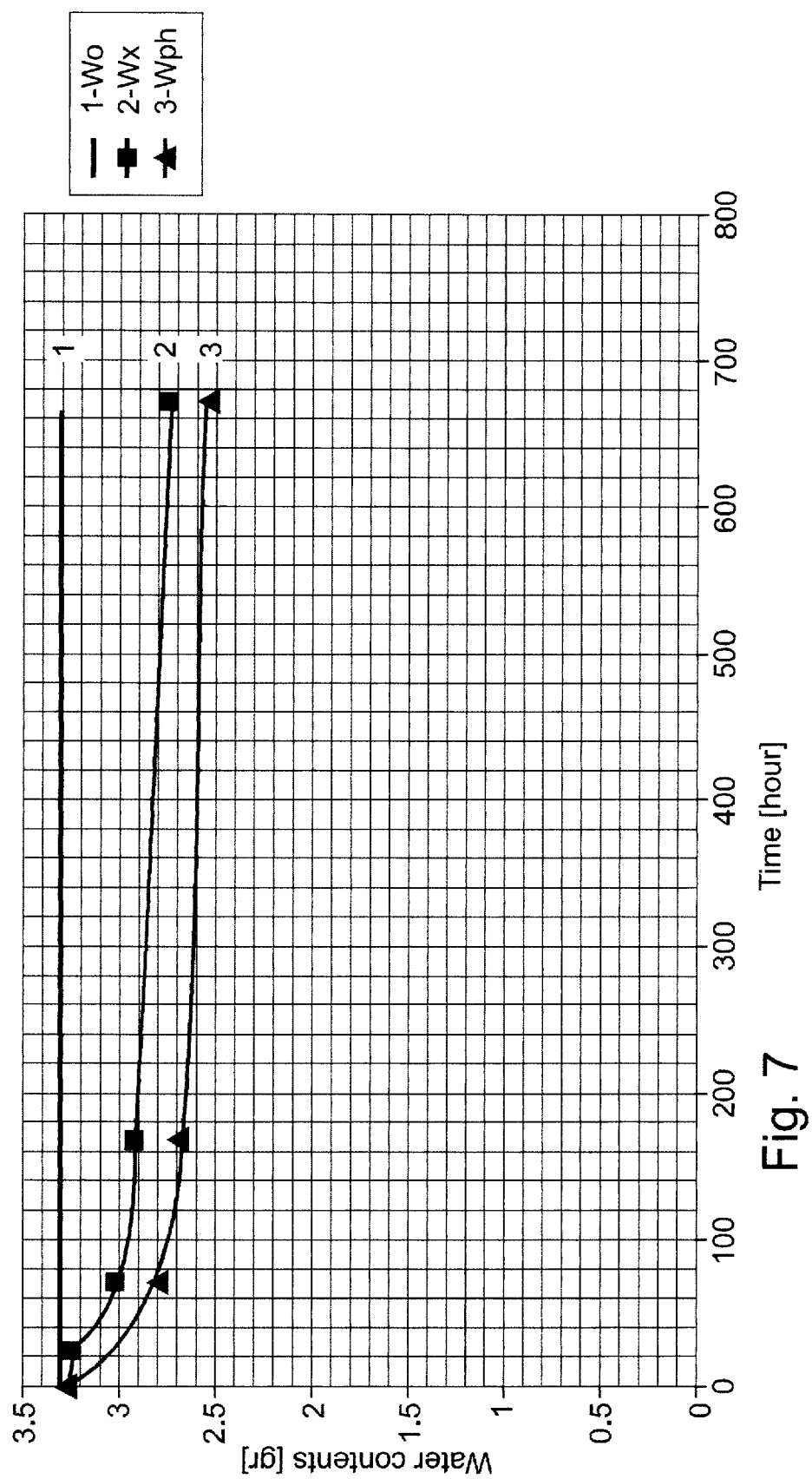
FIG. 7 show plots demonstrating water content during hardening of concrete.

FIG. 7 presents the changes in water masses during the process of hardening of the standard cement-sand mixtures, taking into account the mass of chemically-bound water (Wx).

Since at any moment the overall quantity of water mass (Wo) equals Wx+Wph (wherein, Wph is the mass of physically-bound water, determined by means of NMR-measurements), then, on the basis of the data obtained it follows that not more than 5–7% of the physically-bound water is left "invisible" to the analysis performed.

Figure 5:
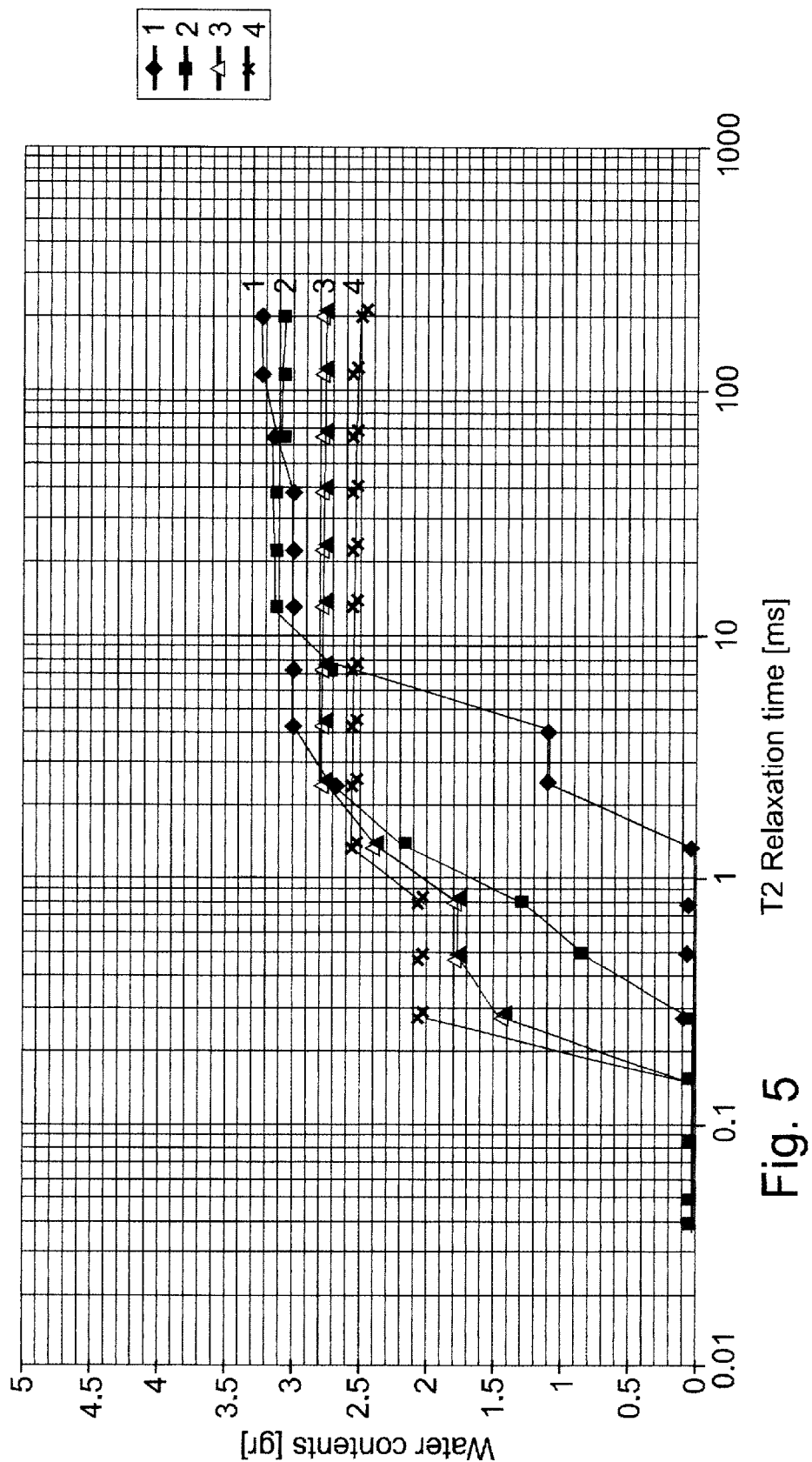
FIG. 5 shows plots demonstrating a linear relationship between amplitudes of spectral curves and water quantity in concrete.
Figure 8:
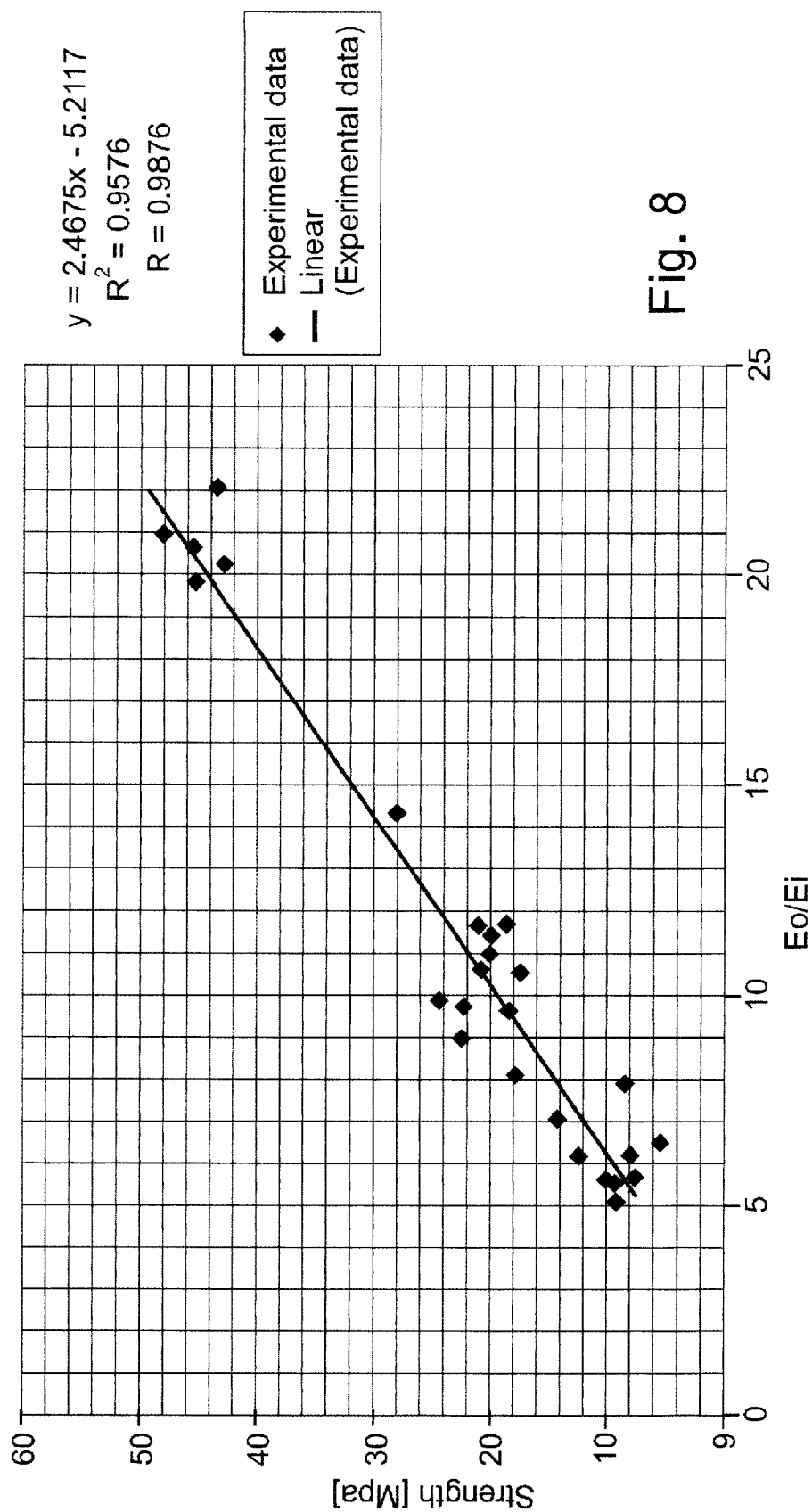
FIG. 8 shows a plot demonstrating a correlation between compressive strength of concrete and relative values of energy absorption in the RF-field.

The absorption energy of the RF-field is determined on the basis of the data presented in FIGS. 5 and 6, by means of equations (3)–(6). As is shown in FIG. 8, the obtained energy values, E, were compared with independently determined standard values of compression strength R (MPa). This comparison revealed a high correlation coefficient (0,9876).

When building the dependencies R=f(E), instead of absolute value of absorption energy, E, of the physically-bound water, the relative value $E_0/Ei$ (FIG. 8) was employed, where $E_0$ is the value of absorption energy of the RF-field, measured at setting start; whereas Ei is the value of absorption energy, measured at setting finish.

The principle advantages of this method is the possibility to measure the relaxation time (and, consequently, energy) continuously during the whole process of hardening or at any of its stages with maximal accuracy of the results obtained, in comparison to other methods.

During the hardening process of cement, concrete and similar capillary-porous chemically active materials, redistribution of physically bound water content, its transformation into a state characterized by higher level of interaction with the solid phase continuously occurs. Since at any moment of time, $t_{(i)}$, the energy state of the water stage is determined by the spectrum of relaxation times, $T_{2(i)}$, then on every spectrogram it is possible to select several signal packets—spectra with particular relaxation times; each spectrum corresponds to a particular quantity of water content, having a level energy E.

The general energy balance at time t is determined by:

$$ER(tj) = \sum_{i=1}^{i=n} N_i T_{2(i)} \tag{7}$$

-continued $$E(i) = \text{const} \cdot \Sigma Ni \cdot T_2(i) \tag{8}$$

where i is the number of typical power states of the physically bound water, and which is determined by changes in the $T_2$ relaxation time.

As is shown in FIG. 6, in this case, the value of i changes from 4 at the beginning of the hardening process to 2 following 28 days of hardening.

In performing measurements by high frequency (e.g., at least 7 MHz), spin-echo nuclear magnetic resonance (NMR) according to the present invention at any stage of the hardening process, the relaxation curve-amplitude of the A signal of NMR as a function of the real time, t, is obtained. As a result of mathematical processing of the relaxation curve, the spectrum of $T_2$ relaxation times, that is the set of amplitudes of signals $A_i$ for each relaxation time $T_{2(i)}$ is:

$$A(t) = \sum_{i=1}^{i=n} A_i e^{(t/T_{2(i)})} \tag{9}$$

While processing the experimental curves of spectra of the $T_2$ relaxation times and in order to increase accuracy of obtained results, i=16 was used. In the most simple case the exponent in equation (9) is i=2, wherein the first exponent, i.e., i=1, is "short", whereas, the second exponent, i.e., i=2, is "long". As a result, the "short" exponent defines the physically bound water having strong interactions with the cement structure, whereas, the "long" exponent defines the physically bound water having weaker interactions therewith.

Figure 9:
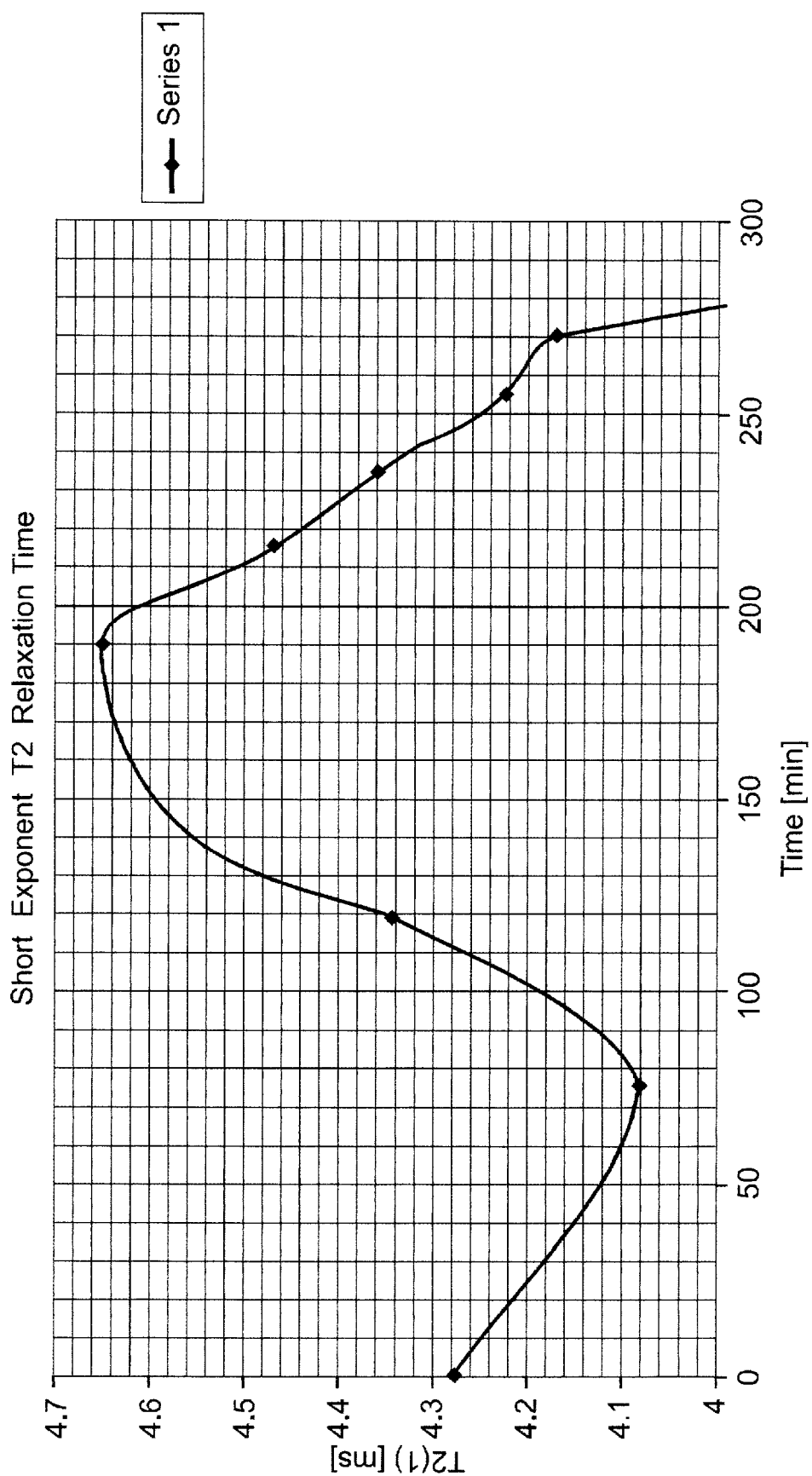
FIG. 9 shows a plot demonstrating the determination of setting start point of cement according to results of measurements of a "short" exponent $T_2$ relaxation time.
Figure 10:
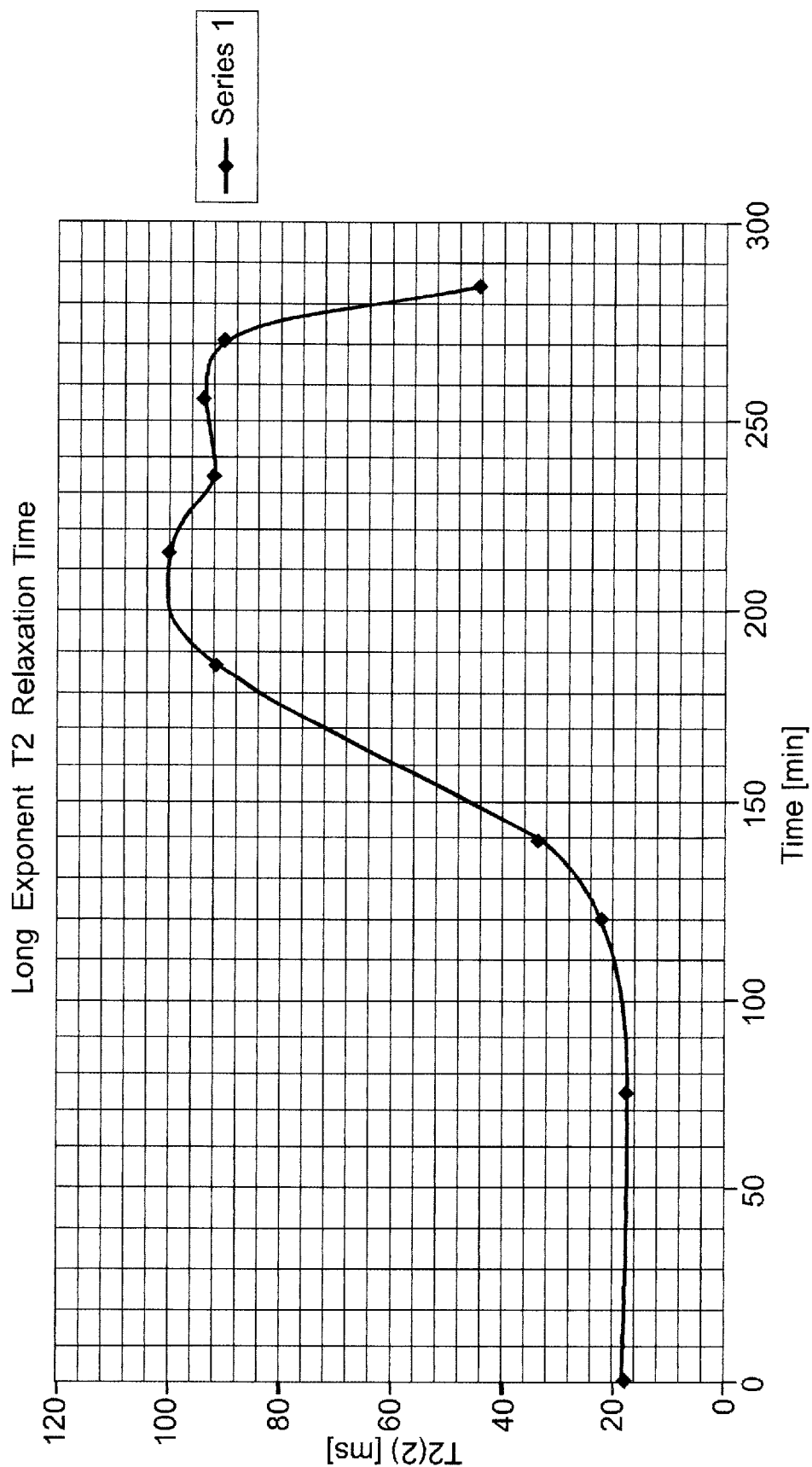
FIG. 10 shows a plot demonstrating the determination of setting finish point of cement according to results of measurements of a "long" exponent $T_2$ relaxation time.

FIGS. 9 and 10 present curves of "short" and "long" exponent measured at the starting stage of hardening of the standard cement-sand mixtures. It is obvious, that the obtained curves are characterized by local minima and/or maxima, which enable one to correlate such curves with the setting times of cement. It will be appreciated that the first maximum of the curve representing the first or "short" exponent (FIG. 9) defines the setting start time. It will further be appreciated that the point of dramatic decline in the second or "long" exponent (FIG. 10) defines the setting finish time.

After the determination of the corresponding value of strength $R_j$ at every time $t_j$, the correlation dependency "strength-energy" is obtained. Since the energy is a fundamental parameter of the substance state, then the dependency R=f(E) is universal and can be applied for the determination of the strength of cement and concrete of different contents $T_2$ at the various stages of hardening.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for measuring a strength of a capillary-porous chemically active material while hardening, the capillary-porous chemically active material including therein water which undergoes stage metamorphosis and including a physically bound water portion having a T2 relaxation time of 30–100 microseconds and a chemically bound water portion having a T2 relaxation time of 10–17 microseconds, the physically bound water portion including water in gel pores and in larger capillaries of the material, the method comprising:

performing a high, at least 7 MHz frequency, spin-echo nuclear magnetic resonance measurement of at least said physically bound water portion; and correlating said high frequency, spin-echo nuclear magnetic resonance measurement with a predetermined relationship between said strength and said high frequency, spin-echo nuclear magnetic resonance measurement;

wherein, said predetermined relationship is based on:
(i) linear relation between a quantity of said physically bound water in the material and an amplitude of said spin-echo nuclear magnetic resonance measurement generated by said physically bound water; and
(ii) functional dependency between an energy state of water, as determined by an overall energy of absorption of an RF field, and a relaxation time of water.

2. The method of claim 1, wherein a radio frequency shield is employed to substantially isolate said high frequency, spin-echo nuclear magnetic resonance measurement from environmental noise.

3. A method for measuring a strength of a capillary-porous chemically active material while hardening, the capillary-porous chemically active material including therein water which undergoes stage metamorphosis and including a physically bound water portion having a T2 relaxation time of 30–100 microseconds and a chemically bound water portion having a T2 relaxation time of 10–17 microseconds, the physically bound water portion including water in gel pores and in larger capillaries of the material, the method comprising:

performing a high, at least 7 MHz frequency, spin-echo nuclear magnetic resonance measurements of at least said physically bound water at least at setting start point and at setting finish point; and extrapolating said strength based on a predetermined relationship between said strength and said high frequency, spin-echo nuclear magnetic resonance measurements;

wherein, said predetermined relationship is based on:
(i) linear relation between a quantity of said physically bound water in the material and an amplitude of said spin-echo nuclear magnetic resonance measurement generated by said physically bound water; and
(ii) functional dependency between an energy state of water, as determined by an overall energy of absorption of an RF field, and a relaxation time of water.

4. The method of claim 3, wherein a radio frequency shield is employed to substantially isolate said high frequency, spin-echo nuclear magnetic resonance measurement from environmental noise.

5. A method of measuring a strength of a structure made of concrete while hardening, the concrete including therein physically bound water having a T2 relaxation time of 30–100 microseconds and a chemically bound water portion having a T2 relaxation time of 10–17 microseconds, the physically bound water portion including water in gel pores and in larger capillaries of the concrete, the method comprising:

performing an in situ, high at least 7 MHz frequency, spin-echo nuclear magnetic resonance measurement of at least said physically bound water; and correlating said high frequency, spin-echo nuclear magnetic resonance measurement with a predetermined relationship between said strength and said high MHz frequency, spin-echo nuclear magnetic resonance measurement;

wherein, said predetermined relationship is based on:
(i) linear relation between a quantity of said physically bound water in the material and an amplitude of said spin-echo nuclear magnetic resonance measurement generated by said physically bound water; and
(ii) functional dependency between an energy state of water, as determined by an overall energy of absorption of an RF field, and a relaxation time of water.

6. The method of claim 5, wherein a radio frequency shield is employed to substantially isolate said high frequency, spin-echo nuclear magnetic resonance measurement from environmental noise.

7. A method of predicting a strength of a structure made of concrete while hardening, the concrete including therein physically bound water having a T2 relaxation time of 30–100 microseconds and a chemically bound water portion having a T2 relaxation time of 10–17 microseconds, the physically bound water portion including water in gel pores and in larger capillaries of the concrete, the method comprising:

performing an in situ, a high at least 7 MHz frequency, spin-echo nuclear magnetic resonance measurement of at least said physically bound water; and extrapolating said strength based on a predetermined relationship between said strength and said high frequency, spin-echo nuclear magnetic resonance measurement;

wherein, said predetermined relationship is based on:
(i) linear relation between a quantity of said physically bound water in the material and an amplitude of said spin-echo nuclear magnetic resonance measurement generated by said physically bound water; and
(ii) functional dependency between an energy state of water, as determined by an overall energy of absorption of an RF field, and a relaxation time of water.

8. The method of claim 7, wherein a radio frequency shield is employed to substantially isolate said high frequency, spin-echo nuclear magnetic resonance measurement from environmental noise.

9. An apparatus for measuring a strength of a structure made of a capillary-porous chemically active material while hardening, said capillary-porous chemically active material having a surface and an armature buried in the capillary-porous chemically active material underneath the surface, the capillary-porous chemically active material including therein physically bound water having a T2 relaxation time of 30–100 microseconds and a chemically bound water portion having a T2 relaxation time of 10–17 microseconds, the physically bound water portion including water in gel pores and in larger capillaries of the material, the apparatus comprising a pulsed nuclear magnetic resonance generator for generating a sensitive shallow volume in said concrete structure for performing therein an in situ, high at least 7 MHz frequency, spin-echo nuclear magnetic resonance measurement of at least said physically bound water in the capillary-porous chemically active material while hardening, said pulsed nuclear magnetic resonance generator including in an operative arrangement:

(a) a static magnetic field generator for generating a static magnetic field within said sensitive volume, said static magnetic field generator including at least one magnet so designed such that static magnetic field lines of said static magnetic field are disposable close and substantially perpendicular to said surface;

(b) a radio frequency electromagnetic field generator for generating a radio frequency electromagnetic field, said radio frequency electromagnetic field generator including at least one radio frequency coil so designed such that electromagnetic field lines of said radio frequency electromagnetic field are disposable substantially parallel to said surface, so as to avoid interference with the armature being buried in the capillary-porous chemically active material underneath the surface; and (c) a nuclear magnetic resonance receiver for receiving nuclear magnetic resonance signals form excitable nuclei in said capillary-porous chemically active material and for providing an output indicative of a strength of the capillary-porous chemically active materials.

10. The apparatus of claim 9, wherein each of said at least one radio frequency-coil is shaped as a frustum having a smaller base and a wider top and is disposable with its longitudinal axis perpendicular to said surface and having its smaller base disposable on said surface.

11. The apparatus of claim 9, wherein said at least one magnet includes a horseshoe magnet having its opening disposable against said surface.

12. The apparatus of claim 9, wherein said at least one magnet includes one larger and one smaller horseshoe magnets.

13. The apparatus of claim 9, wherein said at least one magnet has a butterfly-type cross section.

14. The apparatus of claim 9, wherein said at least one magnet includes an upside-down "T"-bar magnet.

15. A method for determining a strength of a capillary-porous chemically active material while hardening, the capillary-porous chemically active material including therein water which undergoes stage metamorphosis and including a portion of physically bound water having a T2 relaxation time of 30–100 microseconds and a chemically bound water portion having a T2 relaxation time of 10–17 microseconds, the physically bound water portion including water in gel pores and in larger capillaries of the material, the method comprising:

performing a spin-echo nuclear magnetic resonance measurement of at least said physically bound water portion; and correlating said spin-echo nuclear magnetic resonance measurement with a predetermined relationship between energy values of said physically bound water and said spin-echo nuclear magnetic resonance measurement, thereby determining the strength of the capillary-porous chemically active material while hardening;

wherein, said predetermined relationship is based on:

(i) linear relation between a quantity of said physically bound water in the material and an amplitude of said spin-echo nuclear magnetic resonance measurement generated by said physically bound water; and (ii) functional dependency between an energy state of water, as determined by an overall energy of absorption of an RF field, and a relaxation time of water.

16. The method of claim 15, wherein a radio frequency shield is employed to substantially isolate said spin-echo nuclear magnetic resonance measurement from environmental noise.

17. A method for determining a strength of a capillary-porous chemically active material while hardening, the capillary-porous chemically active material including therein water which undergoes stage metamorphosis and including a portion of physically bound water having a T2 relaxation time of 30–100 microseconds and a chemically bound water portion having a T2 relaxation time of 10–17 microseconds, the physically bound water portion including water in gel pores and in larger capillaries of the material, the method comprising:

performing spin-echo nuclear magnetic resonance measurements of at least said physically bound water at least at setting start point and at setting finish point; and extrapolating said strength based on a predetermined relationship between said strength and said spin-echo nuclear magnetic resonance measurements;

wherein, said predetermined relationship is based on:

(i) linear relation between a quantity of said physically bound water in the material and an amplitude of said spin-echo nuclear magnetic resonance measurement generated by said physically bound water; and (ii) functional dependency between an energy state of water, as determined by an overall energy of absorption of an RF field, and a relaxation time of water.

18. The method of claim 17, wherein a radio frequency shield is employed to substantially isolate said spin-echo nuclear magnetic resonance measurement from environmental noise.

19. A method of determining a strength of a structure made of concrete, the concrete including therein physically bound water having a T2 relaxation time of 30–100 microseconds and a chemically bound water portion having a T2 relaxation time of 10–17 microseconds, the physically bound water portion including water in gel pores and in larger capillaries of the concrete, the method comprising:

performing an in situ spin-echo nuclear magnetic resonance measurement of at least said physically bound water; and correlating said spin-echo nuclear magnetic resonance measurement with a predetermined relationship between energy values of said physically bound water and said spin-echo nuclear magnetic resonance measurement, thereby determining the strength of the structure made of concrete while hardening;

wherein, said predetermined relationship is based on:

(i) linear relation between a quantity of said physically bound water in the material and an amplitude of said spin-echo nuclear magnetic resonance measurement generated by said physically bound water; and (ii) functional dependency between an energy state of water, as determined by an overall energy of absorption of an RF field, and a relaxation time of water.

20. The method of claim 19, wherein a radio frequency shield is employed to substantially isolate said spin-echo nuclear magnetic resonance measurement from environmental noise.

21. A method of predicting a strength of a structure made of concrete while hardening, the concrete including therein physically bound water having a T2 relaxation time of 30–100 microseconds and a chemically bound water portion having a T2 relaxation time of 10–17 microseconds, the physically bound water portion including water in gel pores and in larger capillaries of the concrete, the method comprising:

performing an in situ spin-echo nuclear magnetic resonance measurement of at least said physically bound water; and extrapolating said strength based on a predetermined relationship between said strength and said spin-echo nuclear magnetic resonance measurement;

wherein, said predetermined relationship is based on:

(i) linear relation between a quantity of said physically bound water in the material and an amplitude of said spin-echo nuclear magnetic resonance measurement generated by said physically bound water; and (ii) functional dependency between an energy state of water, as determined by an overall energy of absorption of an RF field, and a relaxation time of water.

22. The method of claim 21, wherein a radio frequency shield is employed to substantially isolate said spin-echo nuclear magnetic resonance measurement from environmental noise.

23. An apparatus for measuring a strength of a structure made of a capillary-porous chemically active material, the capillary-porous chemically active material having a surface and an armature buried in the capillary-porous chemically active material underneath the surface, the capillary-porous chemically active material including therein physically bound water having a T2 relaxation time of 30–100 microseconds and a chemically bound water portion having a T2 relaxation time of 10–17 microseconds, the physically bound water portion including water in gel pores and in larger capillaries of the concrete, the apparatus comprising a pulsed nuclear magnetic resonance generator for generating a sensitive volume in said concrete structure for performing therein an in situ, spin-echo nuclear magnetic resonance measurement of at least said physically bound water in the capillary-porous chemically active material while hardening, said pulsed nuclear magnetic resonance generator including in an operative arrangement:

(a) a static magnetic field generator for generating a static magnetic field within said sensitive volume, said static magnetic field generator including at least one magnet so designed such that static magnetic field lines of said static magnetic field are disposable close and substantially perpendicular to said surface;

(b) a radio frequency electromagnetic field generator for generating a radio frequency electromagnetic field, said radio frequency electromagnetic field generator including at least one radio frequency coil so designed such that electromagnetic field lines of said radio frequency electromagnetic field are disposable substantially parallel to said surface, so as to avoid interference with the armature being buried in the capillary-porous chemically active material underneath the surface; and (c) a nuclear magnetic resonance receiver for receiving nuclear magnetic resonance signals form excitable nuclei in said capillary-porous chemically active material and for providing an output indicative of a strength of the capillary-porous chemically active materials.

24. The apparatus of claim 23, wherein each of said at least one radio frequency-coil is shaped as a frustum having a smaller base and a wider top and is disposable with its longitudinal axis perpendicular to said surface and having its smaller base disposable on said surface.

25. The apparatus of claim 23, wherein said at least one magnet includes a horseshoe magnet having its opening disposable against said surface.

26. The apparatus of claim 23, wherein said at least one magnet includes one larger and one smaller horseshoe magnets.

27. The apparatus of claim 23, wherein said at least one magnet has a butterfly-type cross section.

28. The apparatus of claim 23, wherein said at least one magnet includes an upside-down "T"-bar magnet.

* * * * *

UNITED STATES PATENT AND TRADEMARK OFFICE
CERTIFICATE OF CORRECTION

PATENT NO. : 6,396,265 B1
DATED : May 28, 2002
INVENTOR(S) : Shtakelberg et al.

It is certified that error appears in the above-identified patent and that said Letters Patent is hereby corrected as shown below:

<u>Title page,</u>
Item [73], Assignee, change Assignee to:
-- Concretec Ltd. --

Signed and Sealed this

Twenty-second Day of October, 2002

*Attest:*

JAMES E. ROGAN
*Director of the United States Patent and Trademark Office*

*Attesting Officer*